United States Patent [19]
Rogers

[11] Patent Number: 5,725,375
[45] Date of Patent: Mar. 10, 1998

[54] ANTI-ROTATIONAL CONNECTING MECHANISM

[75] Inventor: Dan Paul Rogers, Royal Palm Beach, Fla.

[73] Assignee: Implant Innovations, Inc., Palm Beach Gardens, Fla.

[21] Appl. No.: 451,083

[22] Filed: May 25, 1995

[51] Int. Cl.⁶ ........................................ A61C 8/00
[52] U.S. Cl. ............................... 433/172; 433/173
[58] Field of Search .......................... 433/172, 173, 433/174, 175, 176; 403/359, 361; 279/102, 103, 104, 105, 906

[56] References Cited

U.S. PATENT DOCUMENTS

| | | | |
|---|---|---|---|
| 3,958,471 | 5/1976 | Müller | 82/1 |
| 4,011,602 | 3/1977 | Rybicki et al. | 433/173 |
| 5,104,318 | 4/1992 | Piche et al. | 433/173 |
| 5,122,059 | 6/1992 | Dürr et al. | 433/173 |
| 5,195,892 | 3/1993 | Gersberg | 433/173 |
| 5,197,881 | 3/1993 | Chalifoux | 433/173 |
| 5,295,423 | 3/1994 | Mikic | 279/102 |
| 5,334,024 | 8/1994 | Niznick | 433/173 |
| 5,362,234 | 11/1994 | Salazar et al. | 433/173 |
| 5,362,235 | 11/1994 | Daftary | 433/173 |
| 5,417,570 | 5/1995 | Zuest et al. | 433/173 |
| 5,433,606 | 7/1995 | Niznick et al. | 433/173 |
| 5,437,551 | 8/1995 | Chalifoux | 433/173 |

FOREIGN PATENT DOCUMENTS

4028855  3/1992  Germany ................. 433/173

*Primary Examiner*—Cary E. O'Connor
*Attorney, Agent, or Firm*—Arnold, White & Durkee

[57] ABSTRACT

A post-and-socket connector of the anti-rotational kind having means near the base of one or both parts for filling selected portions of the space between them and thereby restricting or eliminating relative rotation of the two parts round a common axis.

28 Claims, 9 Drawing Sheets

ANTI-ROTATIONAL CONNECTING MECHANISM

BACKGROUND OF THE INVENTION

This invention relates to rotation-limiting connecting mechanisms of the kind employing a non-round post engaged in a non-round socket to connect two parts endwise in a fashion that limits relative rotation between the parts around their common axis, as embodied in a dental implant and an abutment, artificial tooth, or another article designed and intended for detachable connection to that implant.

In dental implantology as currently being practiced it is common to use rotation-limiting connecting mechanisms consisting, for example, of a hexagonal post or socket on the implant and a mating socket or post on the article intended to be attached to the implant. There being a wide variety of such articles (posts, copings, artificial teeth, etc..) it is the prevailing manufacturing practice to employ standard sizes of such posts and sockets so that all such articles will fit interchangeably on all available implants of a given manufacturer. The dimensions being used are small. Owing in part to the limitations of manufacturing tolerances, the sockets are a little larger across than the posts, in order to assure that in every case the dentist will be able to put two parts together at chairside, and when necessary to take them apart without difficulty. Typically, the distance between opposing flat surfaces of a hexagonal post may be about 0.0005 inch, more or less, smaller than the distance between opposing flat surfaces of a mating hexagonal socket. While this arrangement provides the essential rotation-limiting connection, it does leave a small amount of rotational looseness, which is undesirable. It does not provide the stability of a natural tooth and, more important, the rotational wiggling which it permits is an environment in which the screw that holds an article fixed to an implant can work itself loose. It is critically important to a successful dental restoration on an implant that the restoration not come loose on the implant.

GENERAL NATURE OF THE INVENTION

Generally in accordance with the invention the post engages initially in the socket entrance loosely as in the prior art, and in one embodiment of the invention the socket has internal means adjacent its bottom for engaging the post more snugly at its free end. In another embodiment of the invention the post has external means near its base for engaging more snugly in the socket near its opening. With this arrangement it is found that when two parts bearing the post and socket are fastened together relative rotation of the parts around their common axis is substantially eliminated, and a true anti-rotational connection is made. As practiced in the customary hexagonal post and socket fittings used in implant dentistry, the socket in the first-named embodiment may have six discreet contact members arrayed one each in the corners between adjacent flat walls which contact the post at each of its corresponding corners, whereas in the second-named embodiment the post may have contact means adjacent its base which contact the socket at least in each of its corners near its mouth. When, for example, an abutment fitted with the improved socket according to the first-named embodiment is fastened to the hexagonal post of an implant with the usual abutment screw little or no relative rotation between the abutment and the implant around their common axis is detected. Similar result is possible when an improved post according to the second-named embodiment is fitted into a hexagonal socket of an implant, for example, and fastened to the implant with an appropriate screw.

BRIEF DESCRIPTION OF THE DRAWINGS

FIG. 2 schematically illustrates the prior art hex post and socket interlock;

DETAILED DESCRIPTION OF THE DRAWINGS

Figure 1:
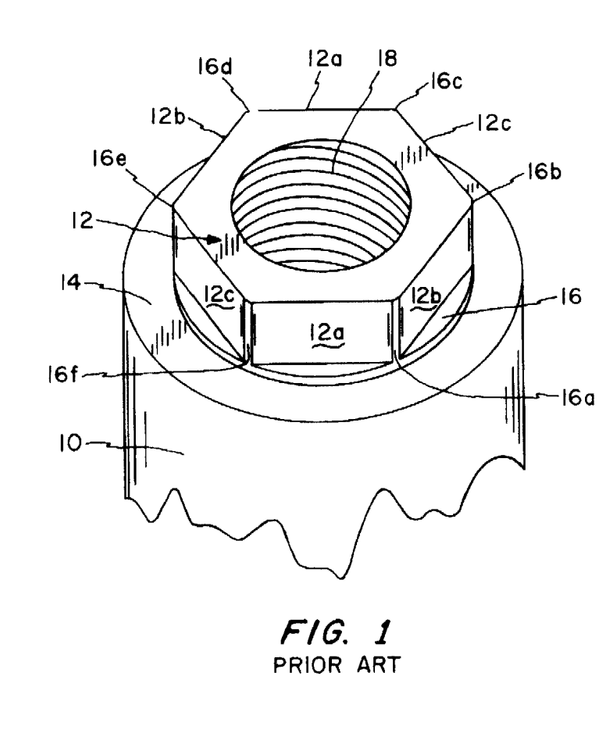
FIG. 1 illustrates in isometric view a typical prior-art rotation-limiting external "hex" post in common use on cylindrical dental implants having a threaded internal bore opening through the hex.

In FIG. 1, a cylindrical dental implant 10 has a hex post 12 on its gingival surface 14. As is common practice at the present time, the hex post 12 has three pairs of opposite parallel flat surfaces 12a, 12b and 12c. These pairs of parallel surfaces may be achieved by straddle-milling an initially cylindrical post 12, leaving a thin round base portion 16 of the initial cylindrical post between the hex and the gingival surface 14. The locus of the initial cylinder remains also in the corner portions 16a–f, inclusive, between adjacent ends of the flat surfaces. A threaded bore 18 in the implant opens through the hex post.

Figures 2A, 2B:
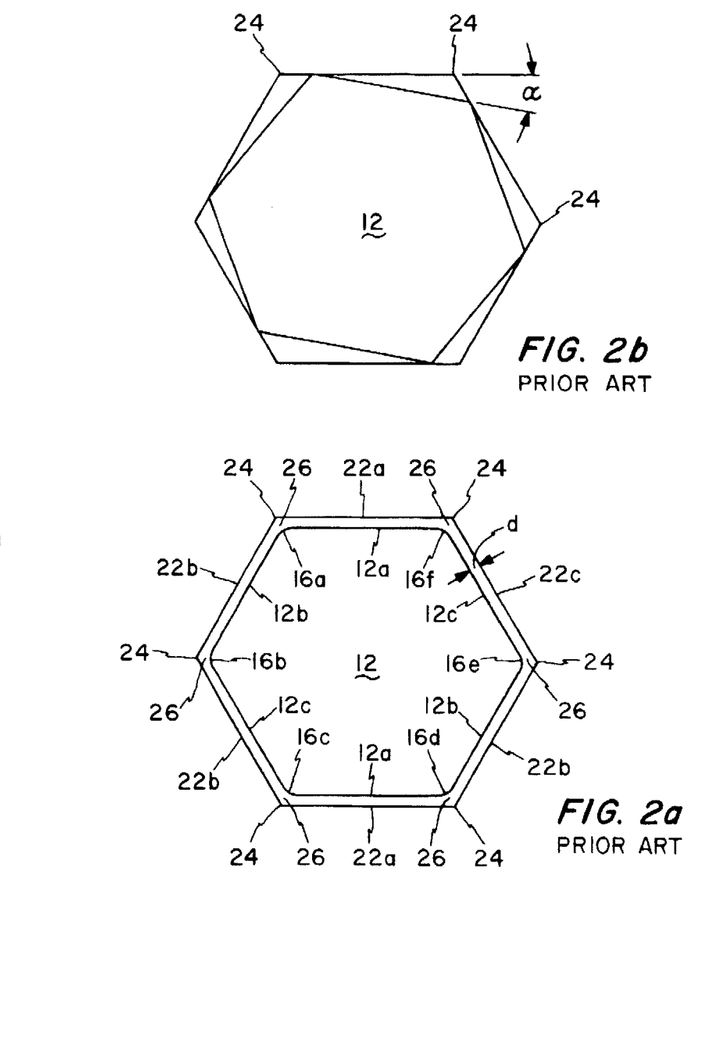
FIGS. 2A schematically illustrates the rotational looseness of the prior art interlock.

FIG. 2 shows, in outline, the hex post of FIG. 1 inside a hexagonal socket. The socket has three pairs of opposite parallel walls 22a, 22b and 22c, adjacent ones of which meet in sharp corners 24. Each of these corners confronts one of the rounded corners 16 a–f of the post 12. The gap distance in each corner is larger than the distance "d" between confronting flat walls, as is shown in the figure, illustrating the rotational looseness of prior art hex post and socket connectors. The consequence of this looseness is illustrated in FIG. 2A, where the angle "a" is the angle through which the post can be turned in one direction or the other in the socket. The extent of looseness is, then, twice the angle "a". The magnitude of the angle "a" depends on the magnitude of the distance "d". In practice, prior art connectors may allow rotational looseness in the range between about 0.75 and 2 or more degrees, in each direction. Such looseness contributes to the loosening, over time, of the screws that are used to fasten dental restorations to dental implants.

Figure 3:
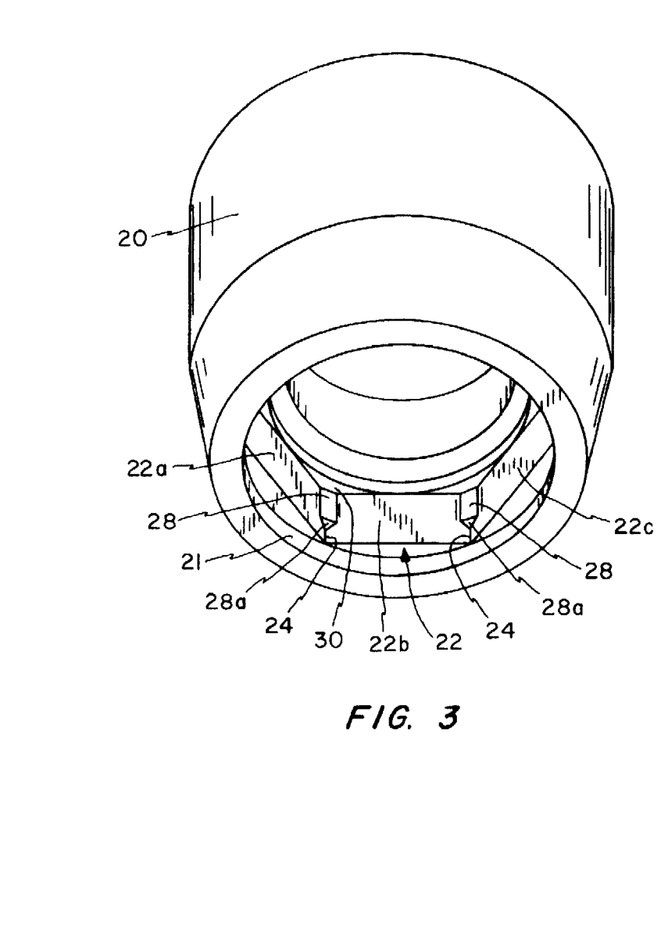
FIG. 3 shows a component having an internal "hex" socket of the invention designed for mating with the prior-art post of FIG. 1.
Figure 4:
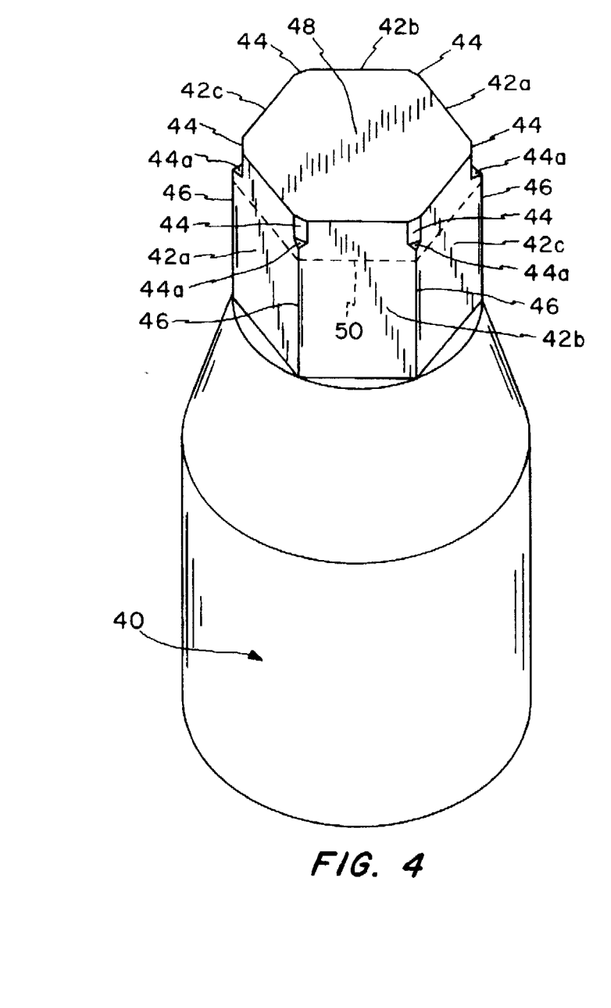
FIG. 4 illustrates a new broach according to the invention for use in making the socket shown in FIG. 3.

In FIG. 3 a component 20 of generally tubular shape has a hexagonal socket 22 sized for mating with the hex post 12. This socket, accordingly, has three pairs of opposite parallel flat surfaces 22a, 22b and 22c, as is illustrated in FIG. 2. It is common practice to make the hexagonal sockets with a broach having sharp edges, which leaves the sharp corners 24 where adjacent flat walls 22a and 22b, or 22b and 22c, meet. In the present invention the corner spaces in the socket 22 are partially filled with corner blocks 28 located one in each corner within the socket near the bottom 30 of the socket. This new socket of the invention may be formed with a new broach 40, shown in FIG. 4. This broach has a tool portion end 48 extending back from which are three pairs of opposite parallel flat surfaces 42a, 42b and 42c, adjacent ones of which meet in sharp corners 46 corresponding respectively to the corners 24 in the socket 22. The tool portion that is used to form the socket is marked by a dashed line 50. The sharp corners 46 of this tool portion are each relieved from the end 48 part way to the line 50 by a longitudinally-oriented flat surface 44 followed by a sloped surface 44a of generally triangular shape the apex of which joins the sharp corner 46. This broach may be used to form the new socket 22 with the corner blocks 38 wherein the sloping triangular surfaces 28a corresponds to the sloped surfaces 44a of the broach. When the component 20 is joined to the implant 10 the corner blocks 28 fill the gaps 26 (FIG. 2) and grip the hex post 12 at its rounded corners 16a–f, inclusive, substantially eliminating the rotational looseness that is characteristic of the prior art. The sloping surfaces 28a facilitate a smooth entrance of the hex post into the restricted region of the socket occupied by the blocks 28

Figure 5:
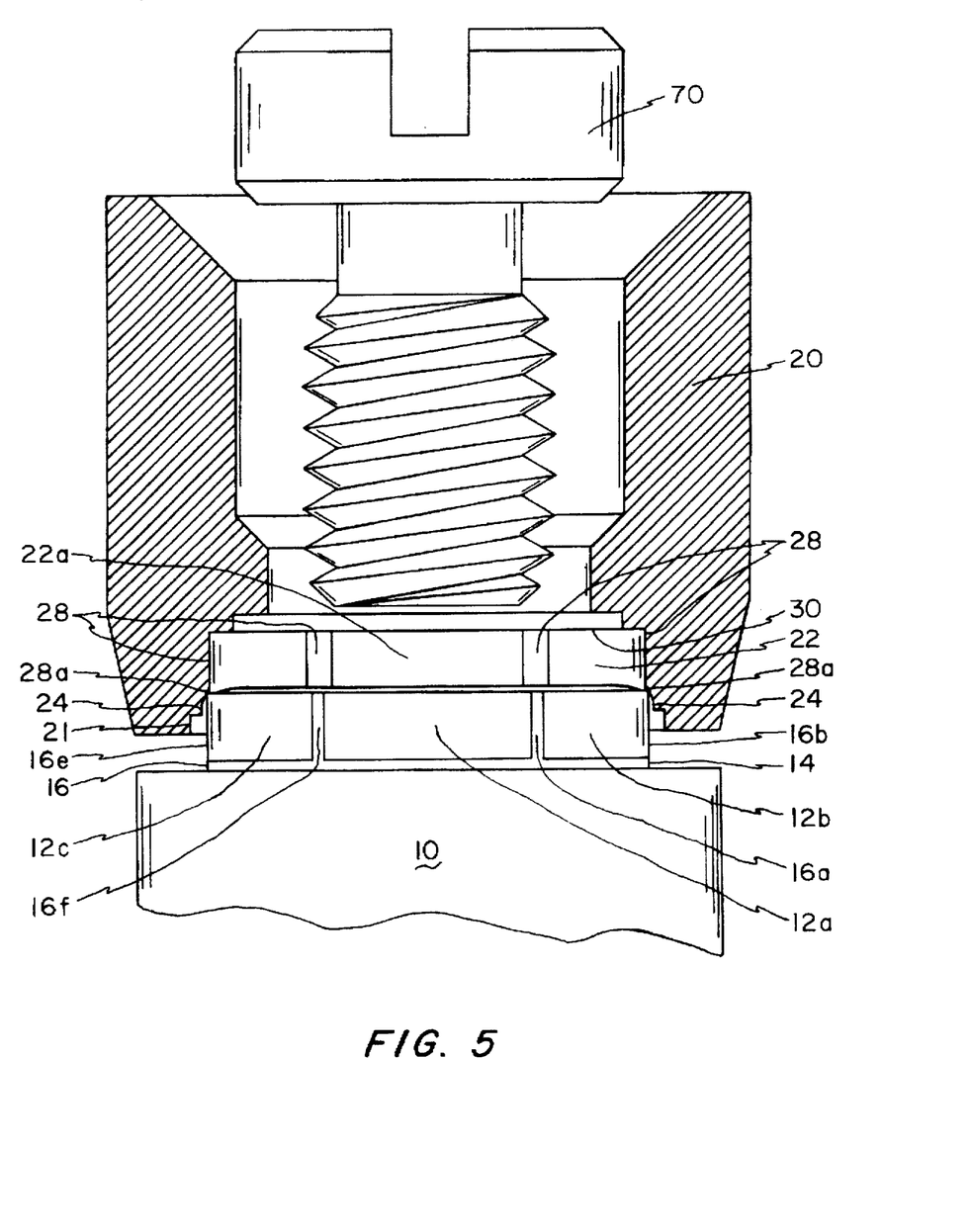
FIG. 5 shows the component of FIG. 3 being mated to the implant of FIG. 1.

FIG. 5 shows how the component 20 and the implant 10 are joined via the hex post 12 and the hex socket 22. Referring to the ring 21, the corners 24, the sloped room for the round base portion 16 of the hex post 12 when the component is seated on the implant surface 14. This ring is followed by the sharp corner portion 24 of the socket which, it will be observed, is spaced away from the hex post 12. This sharp corner portion is followed in turn by the sloped surface 28a of the corner block 28, making a gradual transition from the sharp spaced-away corner to contact between the hex post and the socket. Finally, the block 28 itself comes into firm contact with the hex post at each of the rounded corners 16a–f. The corner blocks can be dimensioned so that opposite pairs of the blocks 28 will squeeze the hex post between them at the corners 16a–f, inclusive. The component can be fastened to the implant with a usual abutment screw 70, for example.

Figure 6A:
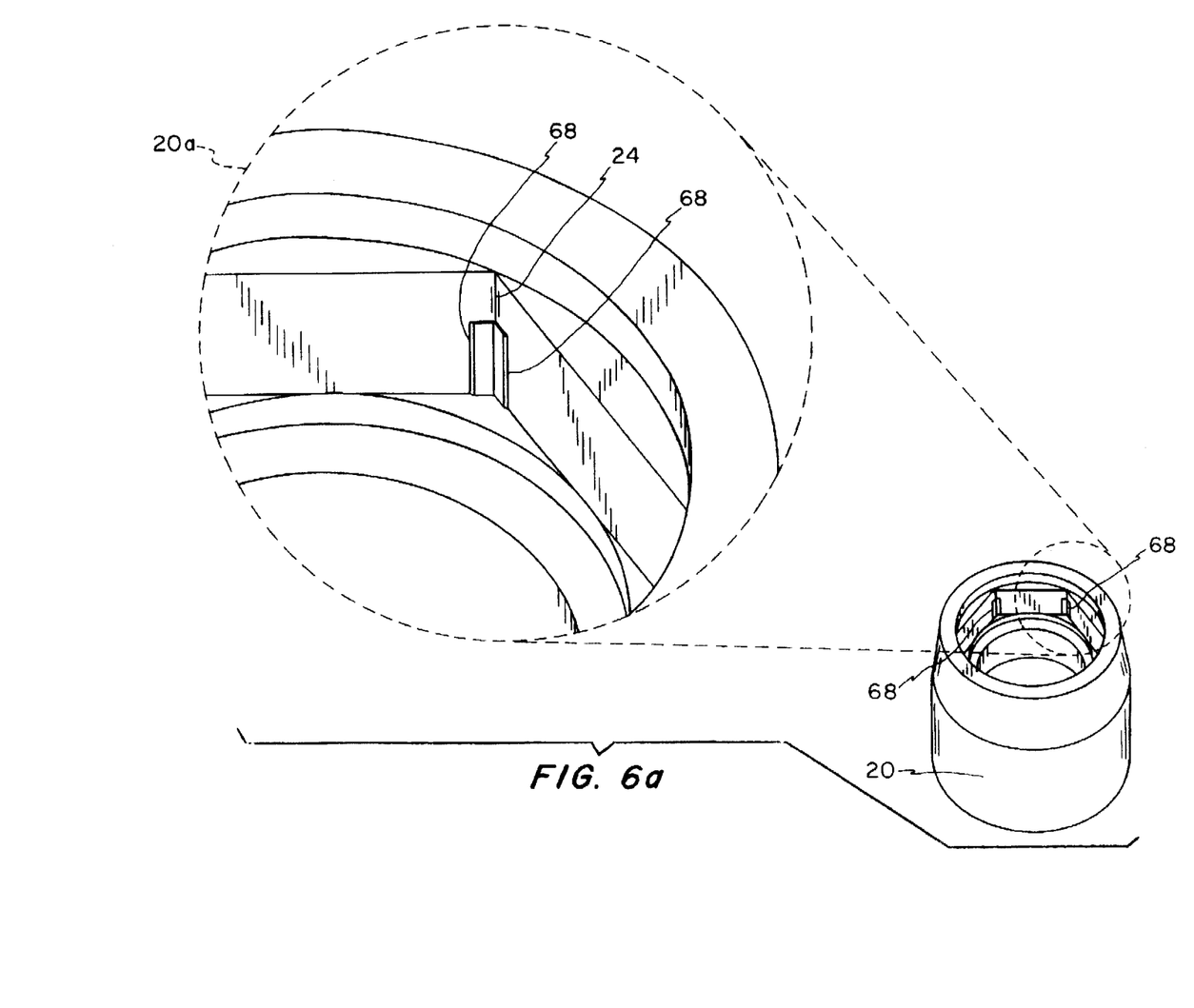
FIGS. 6A–6D show various embodiments of corner blocks.
Figures 6B, 6C, 6D, 6E:
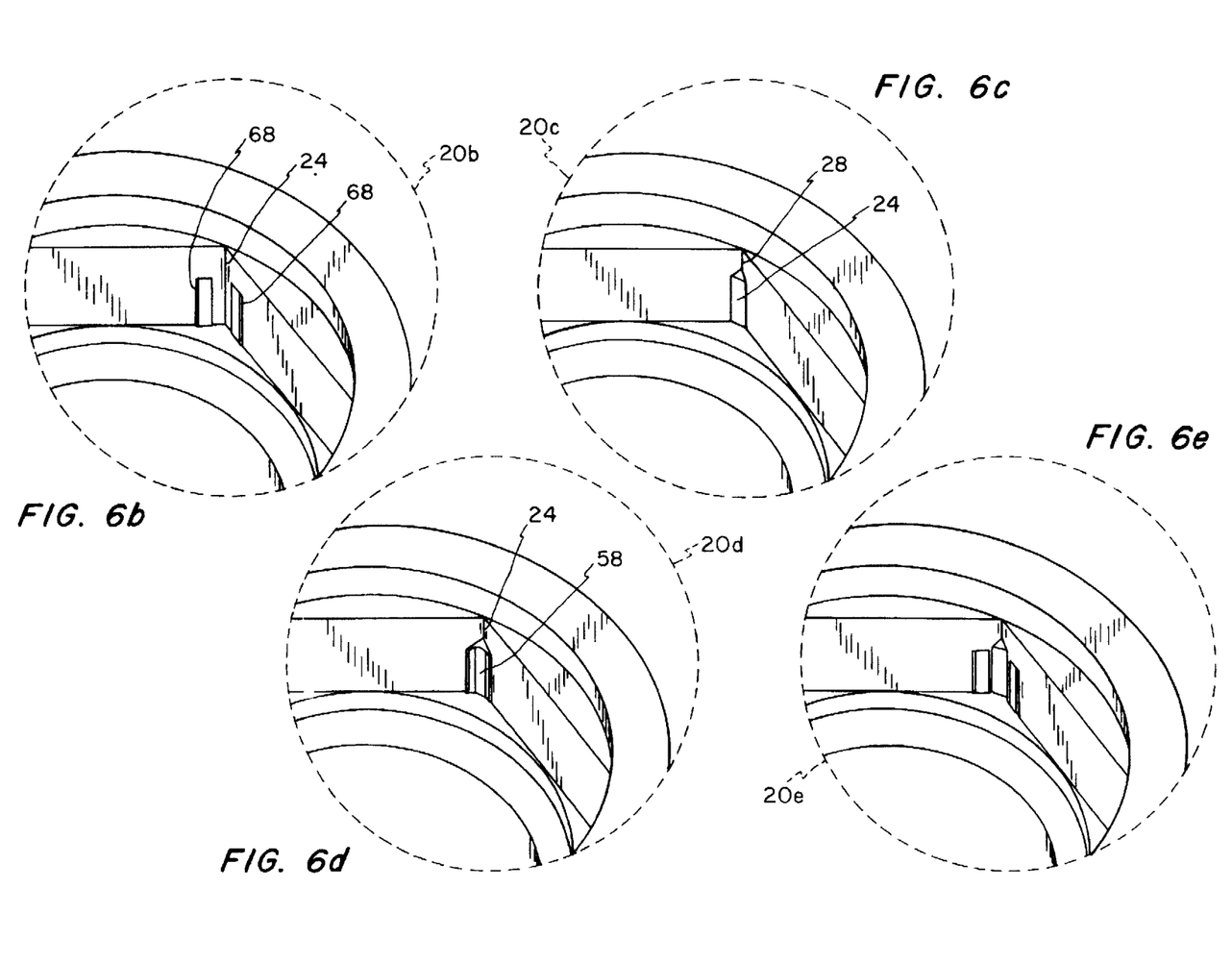
Figure 6F:
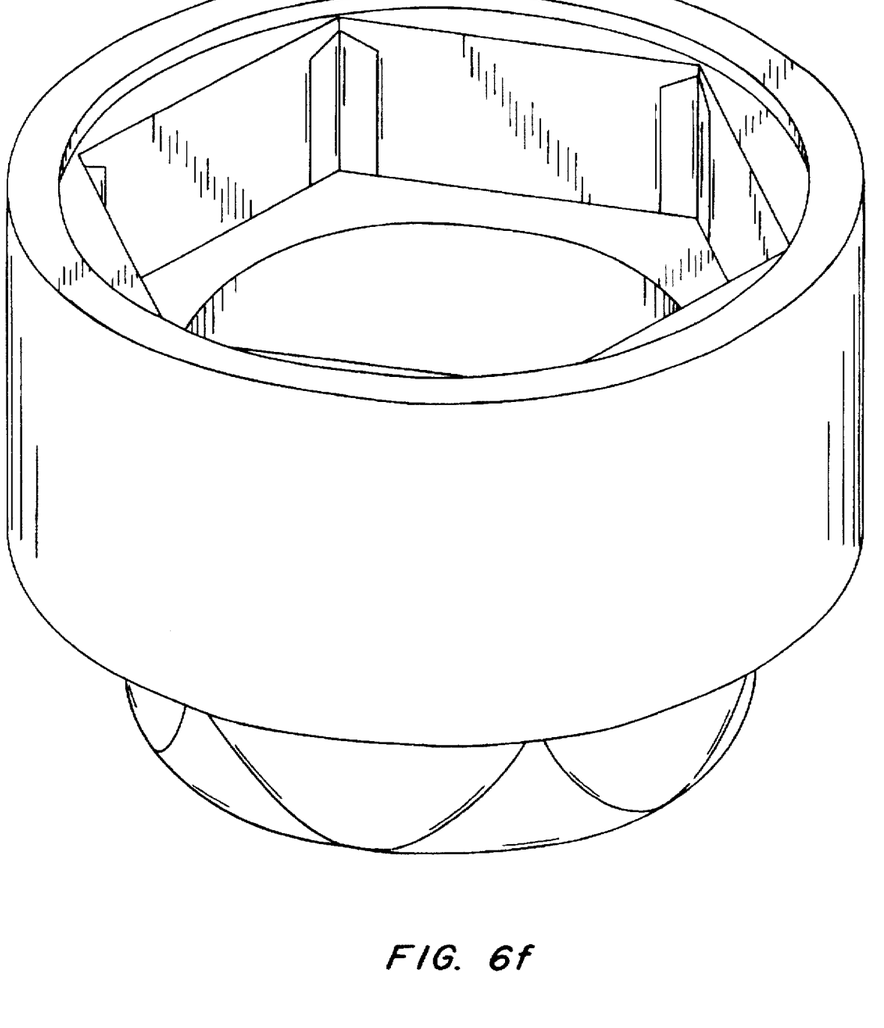
FIG. 6 illustrates additional embodiments of sockets according to the invention.

FIG. 6 shows a modification of the component 20 in which corner shims 68, shown enlarged in a ballon 20a, are substituted for the corner blocks 28 shown in FIG. 3. The shims 68 make contact with sidewalls of a post near a corner to prevent rotatin of the post in the socket, and rely less on squeezing the post between opposing blocks. These shims can be removed somewhat from the corners 24, as is shown in ballon 20b in FIG. 6A. The corner block 28 is shown in ballon 20c (FIG. 6B) for ready comparison. FIG. 6C shows a modified corner block 58 in ballon 20d, designed to combine the side contact of shims 68 with some squeezing effect of the blocks 28. FIG. 6D shows in ballon 20e a corner block 28 accompanied by side shims 68, illustrating still another embodiment of the anti-rotation socket of the invention.

Figure 7A:
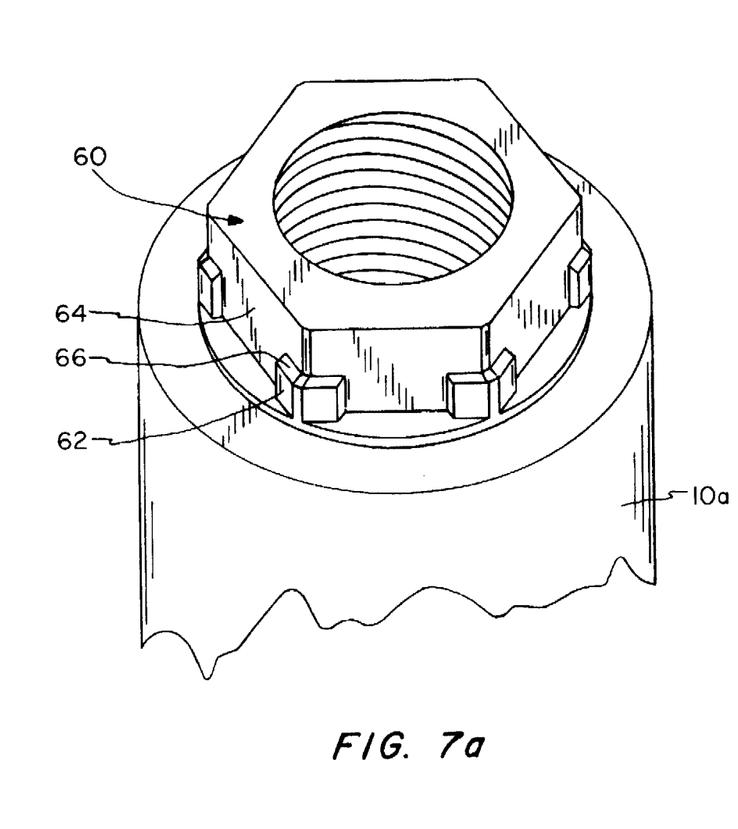
FIG. 7 shows a post modified according to the invention.
Figure 7B:
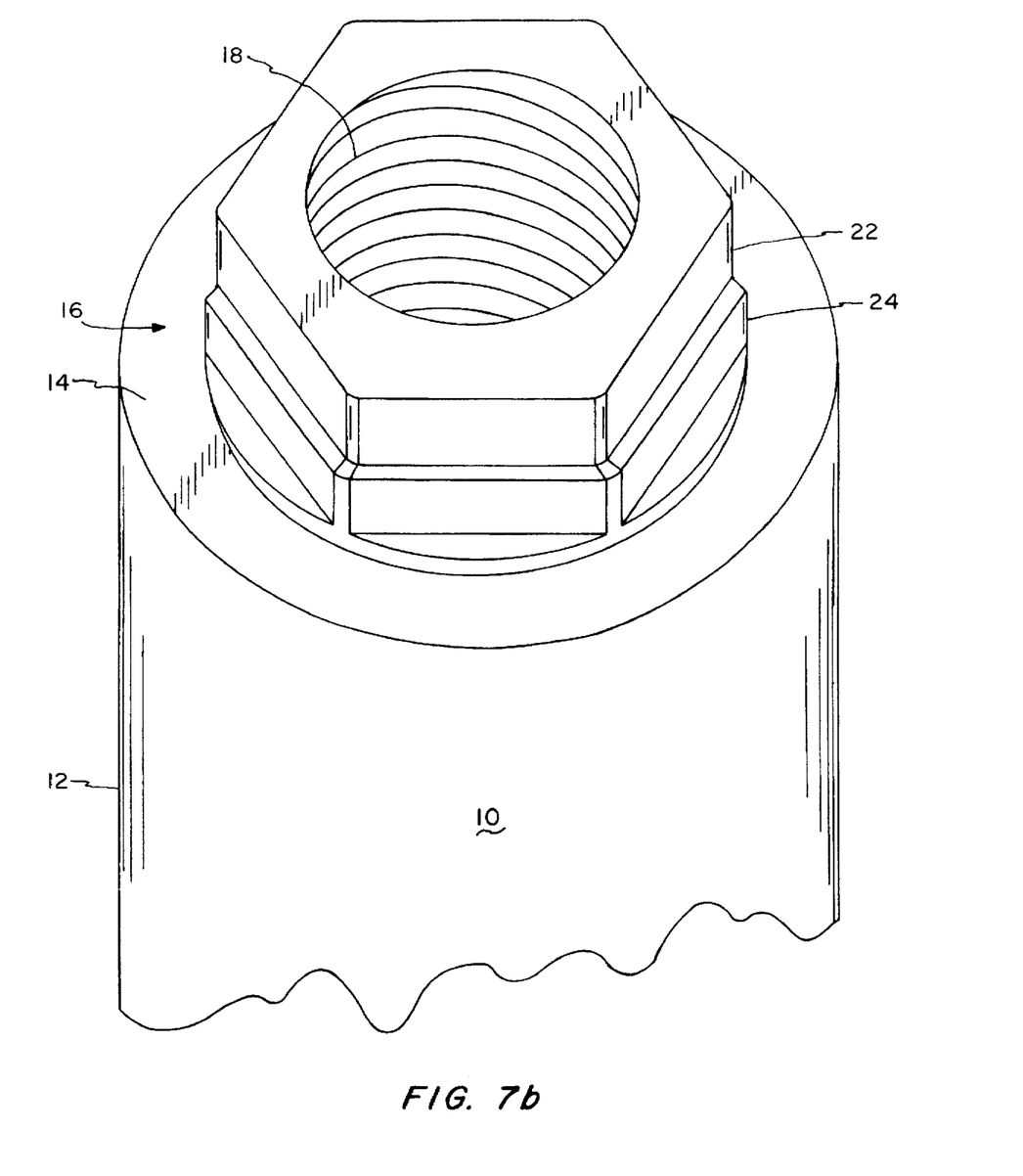
Figure 7C:
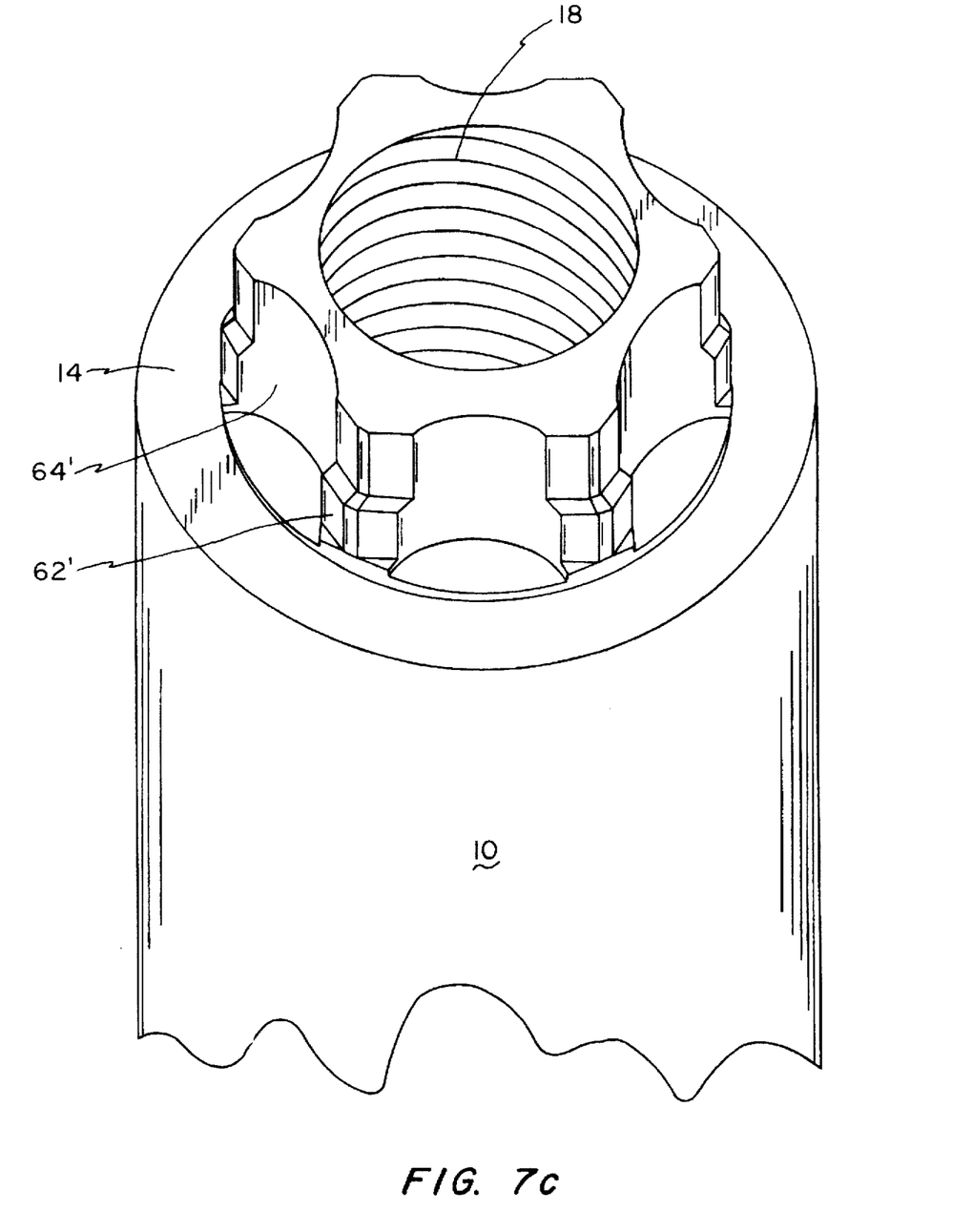

The embodiment of the invention heretofore illustrated and described may be used with abutment posts existing in the prior art. In another embodiment, the hex post may be modified according to the invention, for use with hex sockets existing in the prior art. FIGS. 7 illustrates, by way of example, an implant 10a having a hex post 60 modified according to the present invention. The base portion 62 of this post is made large enough in the corners to fit snugly within the corners of a typical hex socket as found in abutments and other components designed for attachment to dental implant and dental analogs. The enlarged base portions extend only a short distance from the base of the post toward its end. The end portion 64 is smaller "standard"

sized. An intermediate portion 66 on each enlarged corner provides a sloping transition from the base portion 62 to the end portion 64. The end portion 64 fits loosely within available hex sockets. Thus, when the post of the invention is pushed into a hex socket, it will enter easily until the intermediate portion 66 is reached, when force will be required to seat the post in the socket, with the base portion 62 engaging in the corners of the walls of the socket. The required force will be supplied by the screw that is normally used to attach one part to the other. This might be an abutment screw, or a screw or bolt used to mount a transfer coping on an implant or an implant analog, for example. These items being well known, they are not illustrated or described here.

Figure 8:
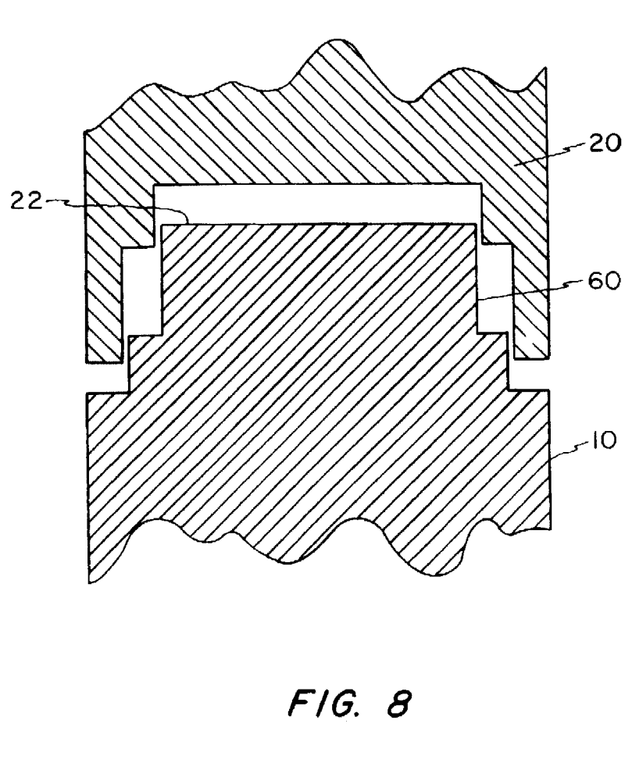
FIG. 8 schematically shows a post and socket according to the invention.

FIG. 8 shows how a post 62 of the invention may be combined with a sockt 22 of the invention to provide a connecting mechanism in two parts each of which embodies the improvement of the invention. Thus, while as in other embodiments illustrated herein the post freely enters the socket, initially, each part will be individually held at an extremity of the invention to provide a connecting mechanism in two parts each of which embodies the improvement of the invention. Thus, while as in other embodiments illustrated herein the post freely enters the socket, initially, each part will be individually held at an extremity when the post is fully seated in the socket.

While the invention has been illustrated in connection with posts and sockets which are currently in use in the field of dental implants, these illustrations are exemplary only. The scope of the invention is defined in the appended claims.

I claim:

1. In a means for connecting a rigid first part to a rigid second part comprising an interlocking post and socket, in which said post extends outwardly along a longitudinal axis from a base of said first part to a free end of said first part and said socket is a recess in said second part extending from an outer end of said second part to a base within said second part one of said parts comprising a dental implant bearing one of said post and socket and the other of said parts comprising a dental component bearing the other of said post and socket, said post having generally flat external sidewalls parallel to said longitudinal axis, said socket having generally flat internal sidewalls parallel to said external sidewalls, said internal and said external sidewalls having non-circular cross sections defining a polygon having a plurality of corners, the improvement wherein upon initial penetration said post fits loosely into said socket and at least one of said post and socket has engagement means on its sidewalls for frictionally engaging the sidewalls of the other in a sliding contact when said free end of said post penetrates further into said socket toward said base of said socket.

2. Connecting means according to claim 1 in which said implant and said component are designed to be connected end-wise with an end wall of one part confronting an end wall of the other part, one of said post and said socket being in one of said end walls, and the other of said post and said socket being in the other of said end walls.

3. Connecting means according to claim 2 in which said implant comprises a body portion that is cylindrical in form and said post-and-socket restrict rotation of said component around the axis of said body portion.

4. In a means for connecting a rigid first part to a rigid second part comprising an interlocking post and socket, in which said post extends outwardly along a longitudinal axis from a base of said first part to a free end of said first part and said socket is a recess in said second part extending from an outer end of said second part to a base within said second part, one of said parts comprising a dental implant bearing one of said post and socket and the other of said parts comprising a dental component bearing the other of said post and said socket, said post having generally flat external sidewalls parallel to said longitudinal axis, said socket having generally flat internal sidewalls parallel to said external sidewalls, said internal and said external sidewalls each having a cross-sectional shape defining a hexagon including six corner regions, said corner regions including a corner of said hexagon and a portion of said sidewall adjacent said corner, the improvement wherein upon initial penetration said post fits loosely into said socket and at least one of said post and socket has six discrete engagement elements located one at each of said corner regions adjacent said base for frictionally engaging the sidewalls of the other in a sliding contact when said free end of said post penetrates further into said socket toward said base of said socket.

5. Connecting means according to claim 4 in which said implant and said component are designed to be connected end-wise with an end wall of one part confronting an end wall of the other part, one of said post and said socket being on one of said end walls, and the other of said post and said socket being in the other of said end walls.

6. Connecting means according to claim 5 in which said implant comprises a body portion that is cylindrical in form and said post-and-socket restrict rotation of said component around the axis of said body portion.

7. In a cutting tool comprising a shaft, a distal end, and a cutting end section comprising transverse cutting edges in a polygonal array with side wall surfaces extending along said shaft a prescribed distance from said distal end for forming in a host body a corresponding polygonal socket with interior walls and a prescribed depth, an improvement in the end section of said tool which includes said cutting edges and is limited to less than said depth of said socket, wherein at least a portion of the side walls of said shaft in said end section is indented to provide corresponding projections extending from said interior walls within said socket.

8. A cutting tool according to claim 7 having a plurality of discrete indentations arrayed around said tool at said cutting edges for forming discrete projections in said socket.

9. A cutting tool according to claim 8 in which said indentations are limited to those regions of said tool where adjacent side walls meet.

10. A cutting tool according to claim 8 in which said indentations have uniformly the same depth.

11. A dental implant system comprising an implant and an abutment having an interlocking post and socket, in which said post extends outwardly along a longitudinal axis from a base of said implant to a free end of said implant and said socket is a recess in said abutment extending inwardly from an outer end of said abutment to a base within said abutment, said post comprising a plurality of generally flat external sidewalls parallel to said longitudinal axis and meeting at corners, said socket comprising a corresponding plurality of generally flat internal sidewalls parallel to said longitudinal axis and meeting in corners, the improvement wherein said post and said socket are dimensioned so that said post fits loosely into said socket upon initial penetration and at least one of said post and socket has engagement means extending from its sidewalls to frictionally engage a portion of the generally flat sidewalls of the other in a sliding contact when said free end of said post penetrates further into said socket toward said base of said socket.

12. A dental implant system comprising an implant and an abutment having an interlocking post and socket, in which said post extends outwardly along a longitudinal axis from a base of said abutment to a free end of said abutment and said socket is a recess in said implant extending inwardly from an outer end of said implant to a base within said implant, said post comprising a plurality of generally flat external sidewalls parallel to said longitudinal axis and meeting at corners, said socket comprising a corresponding plurality of generally flat internal sidewalls parallel to said longitudinal axis and meeting in corners, the improvement wherein said post and said socket are dimensioned so that said post fits loosely into said socket upon initial penetration and at least one of said post and socket has engagement means extending from its sidewalls to frictionally engage a portion of the generally flat sidewalls of the other in a sliding contact when said free end of said post penetrates further into said socket toward said base of said socket.

13. A dental implant system comprising an implant and an abutment having an interlocking post and socket, in which said post extends outwardly along a longitudinal axis from a base of said implant to a free end of said implant and said socket is a recess in said abutment extending inwardly from an outer end of said abutment to a base within said abutment, said post comprising a plurality of rigid and generally flat external sidewalls parallel to said longitudinal axis and meeting at corners, said socket comprising a corresponding plurality of generally flat internal sidewalls parallel to said longitudinal axis and meeting in corners, the improvement wherein said post and said socket are dimensioned so that said post fits loosely into said socket upon initial penetration and at least one of said post and socket has engagement means extending from its sidewalls to form an anti-rotational connection with the other of said post and socket when said free end of said post penetrates further into said socket toward said base of said socket.

14. A dental implant system according to claim 13 wherein said engagement means comprise a plurality of discrete engagement elements positioned non-continuously about the periphery of the sidewalls of at least one of said post and socket.

15. A dental implant system according to claim 14 in which said plurality of engagement elements are positioned in regions including said corners of said socket.

16. A dental implant system according to claim 14 in which said plurality of engagement elements are positioned in regions including said corners of said post.

17. A dental implant system comprising an implant and an abutment having an interlocking post and socket, in which said post extends outwardly along a longitudinal axis from a base of said abutment to a free end of said abutment and said socket is a recess in said implant extending inwardly from an outer end of said implant to a base within said implant, said post comprising a plurality of rigid and generally flat external sidewalls parallel to said longitudinal axis and meeting at corners, said socket comprising a corresponding plurality of generally flat internal sidewalls parallel to said longitudinal axis and meeting in corners, the improvement wherein said post and said socket are dimensioned so that said post fits loosely into said socket upon initial penetration and at least one of said post and socket has engagement means extending from its sidewalls to form an anti-rotational connection with the other of said post and socket when said free end of said post penetrates further into said socket toward said base of said socket.

18. A dental implant system according to claim 17 wherein said engagement means comprise a plurality of discrete engagement elements positioned non-continuously about the periphery of the sidewalls of at least one of said post and socket.

19. A dental implant system according to claim 18 in which said plurality of engagement elements are positioned in regions including said corners of said socket.

20. A dental implant system according to claim 18 in which said plurality of engagement elements are positioned in regions including said corners of said post.

21. A dental implant system comprising an implant and an abutment having interlocking elements forming a post and a socket, said post extending outwardly along a longitudinal axis from a base of said implant to a free end of said implant and said socket extending inwardly from an outer end of said abutment to a base within said abutment, each of said interlocking elements forming a plurality of rigid and generally flat external sidewalls parallel to said longitudinal axis and meeting at corners, said socket comprising a corresponding plurality of generally flat internal sidewalls parallel to said longitudinal axis and meeting in corners, at least one of said interlocking elements having anti-rotation means projecting from its sidewalls toward the sidewalls of the other interlocking element and extending parallel to said longitudinal axis, said interlocking elements being dimensioned so that said post fits loosely into said socket upon initial penetration and then more tightly to form an anti-rotational connection upon full penetration.

22. A dental implant system according to claim 21 wherein said anti-rotation means comprise a plurality of discrete anti-rotation elements positioned in corner regions of at least one of said post and socket, each of said corner regions including a corner and two adjoining sidewall regions extending from said corner a distance less than about half the distance to an adjacent corner.

23. A dental implant system according to claim 22 in which said plurality of discrete anti-rotation elements are positioned in said corner regions of said socket and include a tapered upper surface to facilitate smooth entry of said post into said socket.

24. A dental implant system according to claim 22 in which said plurality of discrete anti-rotation elements are positioned in said corner regions of said post and include a tapered upper surface to facilitate smooth entry of said post into said socket.

25. A dental implant system comprising an implant and an abutment having interlocking elements forming a post and a socket, said post extending outwardly along a longitudinal axis from a base of said abutment to a free end of said abutment and said socket extending inwardly from an outer end of said implant to a base within said implant, each of said interlocking elements forming a plurality of rigid and generally flat external sidewalls parallel to said longitudinal axis and meeting at corners, said socket comprising a corresponding plurality of generally flat internal sidewalls parallel to said longitudinal axis and meeting in corners, at least one of said interlocking elements having anti-rotation means projecting from its sidewalls toward the sidewalls of the other interlocking element and extending parallel to said longitudinal axis, said interlocking elements being dimensioned so that said post fits loosely into said socket upon initial penetration and then more tightly to form an anti-rotational connection upon full penetration.

26. A dental implant system according to claim 25 wherein said anti-rotation means comprise a plurality of discrete anti-rotation elements positioned in corner regions of at least one of said post and socket, each of said corner regions including a corner and two adjoining sidewall regions extending from said corner a distance less than about half the distance to an adjacent corner.

27. A dental implant system according to claim 26 in which said plurality of discrete anti-rotation elements are positioned in said corner regions of said socket and include a tapered upper surface to facilitate smooth entry of said post into said socket.

28. A dental implant system according to claim 26 in which said plurality of discrete anti-rotation elements are positioned in said corner regions of said post and include a tapered upper surface to facilitate smooth entry of said post into said socket.

* * * * *